United States Patent
Sinko et al.

(10) Patent No.: US 9,566,349 B2
(45) Date of Patent: Feb. 14, 2017

(54) INTESTINAL PEPTIDE TARGETING LIGANDS

(71) Applicant: Rutgers, The State University of New Jersey, New Brunswick, NJ (US)

(72) Inventors: Patrick J. Sinko, Annandale, NJ (US); Xiaoping Zhang, Piscataway, NJ (US); Zoltan Szekely, New Brunswick, NJ (US)

(73) Assignee: RUTGERS, THE STATE UNIVERSITY OF NEW JERSEY, New Brunswick, NJ (US)

( * ) Notice: Subject to any disclaimer, the term of this patent is extended or adjusted under 35 U.S.C. 154(b) by 0 days.

(21) Appl. No.: 14/592,489

(22) Filed: Jan. 8, 2015

(65) Prior Publication Data

US 2015/0202322 A1   Jul. 23, 2015

Related U.S. Application Data

(63) Continuation-in-part of application No. 14/445,541, filed on Jul. 29, 2014, which is a continuation of application No. 13/879,205, filed as application No. PCT/US2011/056449 on Oct. 14, 2011, now Pat. No. 8,791,234.

(60) Provisional application No. 61/393,072, filed on Oct. 14, 2010.

(51) Int. Cl.
| | |
|---|---|
| A61K 47/48 | (2006.01) |
| C07K 7/06 | (2006.01) |
| C07K 7/08 | (2006.01) |
| A61K 45/06 | (2006.01) |
| A61K 38/08 | (2006.01) |
| C07K 17/14 | (2006.01) |

(52) U.S. Cl.
CPC ......... *A61K 47/48869* (2013.01); *A61K 38/08* (2013.01); *A61K 45/06* (2013.01); *A61K 47/48215* (2013.01); *A61K 47/48238* (2013.01); *A61K 47/48907* (2013.01); *C07K 7/06* (2013.01); *C07K 7/08* (2013.01); *C07K 17/14* (2013.01)

(58) Field of Classification Search
None
See application file for complete search history.

(56) References Cited

U.S. PATENT DOCUMENTS 8,791,234 B2 * 7/2014 Sinko et al. .......... 530/327
2009/0221482 A1 * 9/2009 Cerami et al. ......... 514/12

FOREIGN PATENT DOCUMENTS

| WO | 2008/084899 | 7/2008 | |
| WO | WO 2008084899 | * 7/2008 | ............... C07K 7/00 |

OTHER PUBLICATIONS

Sapra, et al., "Ligand-targeted liposomes for cancer treatment", Curr Drug Deliv 2,369-81 (2005), abstract.*
Gregoriadis et al., "Improving the therapeutic efficiacy of peptides and proteins: a role for polysialic acids," Intl J Pharm, Aug. 2005, vol. 300, No. 1-2, pp. 125-130 (Abstract only).
Gregoriadis and Ryman, Liposomes as carriers of enzymes or drugs: a new approach to the treatment storage diseases,: Biochem J, 1971, vol. 124, p. 58P.
Hermanson, G, Bioconjugate Techniques, 1996, Elsevier Inc. (Synopsis only).
Sapra et al., "Ligand-targeted liposomes for cancer treatment," Curr Drug Deliv, 2005, vol. 2, pp. 369-381 (Abstract only).
Sarmento et al., Oral insulin delivery by means of solid lipid nanoparticles,: Int. J. Nanomedicine, 2007, vol. 2, No. 4, pp. 743-749.
Written Opinion of the International Searching Authority for PCT/US2011/056449 dated Jan. 31, 2012.
International Search Report for PCT/US2011/056449 dated Jan. 31, 2012.
International Preliminary Report on Patentability for PCT/US2011/056449 dated Feb. 18, 2014.
U.S. Appl. No. 14/445,541, filed Jul. 29, 2014, Intestinal Peptide Targeting Ligands.
U.S. Appl. No. 13/879,205, filed Jul. 30, 2013, Intestinal Peptide Targeting Ligands.

* cited by examiner

*Primary Examiner* — Maury Audet
(74) *Attorney, Agent, or Firm* — Fox Rothschild LLP

(57) ABSTRACT

Peptide ligands for transporting therapeutic agents across the intestinal epithelial barrier that ordinarily are inadequately absorbed and must be delivered by alternative means, which contain an isolated amino acid sequence wherein at least one pair of amino acids are of an opposite charge and the pair members are separated by a spacer of 1-12 amino acid residues including at least one hydrophobic amino acid, and wherein the length of the amino acid sequence is greater than 5 and less than 20 amino acids. Pharmaceutical compositions for gastro-intestinal delivery and methods for the gastrointestinal delivery of poorly absorbed therapeutic agents are also disclosed.

23 Claims, 2 Drawing Sheets

ApoB48 levels in the basolateral medium of Caco-2 monolayer fractioned by ultracentrifugation. Cells were incubated with phage displaying 19 peptide or a negative 15 peptide

INTESTINAL PEPTIDE TARGETING LIGANDS

CROSS-REFERENCE TO RELATED APPLICATIONS

This application is a continuation in part of U.S. patent application Ser. No. 14/445,541, which claims priority to U.S. Pat. No. 8,791,234 (Ser. No. 13/879,205), which claims priority to U.S. Provisional Patent Application Ser. No. 61/393,072, filed on Oct. 14, 2010, the disclosure of which is incorporated herein by reference in its entirety.

GOVERNMENT SUPPORT

This invention was made with government support under AI051214 awarded by the National Institutes of Health. The federal government has certain rights in this invention.

FIELD OF THE INVENTION

The present invention relates to peptide ligands that facilitate transport of agents and carriers across the intestinal epithelial barrier, which are useful for, inter alia, improving oral delivery and intestinal absorption of therapeutic, biologic and diagnostic agents.

BACKGROUND OF THE INVENTION

Oral delivery of therapeutic macromolecular drugs such as peptides, proteins (e.g. insulin) and siRNAs, as well as many small molecules without natural intestinal carriers, has been challenging. While such drugs offer promising therapeutic value, when orally administered many fail to be adequately transported from the patient's gastrointestinal tract to the bloodstream. Thus, very little of the drug is actually absorbed and bioavailable for its intended therapeutic purpose.

As a result, there is a continuing need in the art for novel mechanisms of achieving increased drug absorption and bioavailability in the oral delivery context. This is particularly true with macromolecular drugs and other known biologics.

SUMMARY OF THE INVENTION

The instant invention addresses the foregoing need. Peptide ligands have now been discovered that transport therapeutic agents across the intestinal epithelial barrier that ordinarily are inadequately absorbed and must be delivered by alternative means.

One aspect of the present invention provides a conjugate comprising one or more peptide ligands attached to a nanoparticle carrier. The nanoparticle carrier comprises a hydrophobic therapeutic agent admixed with a biocompatible block copolymer comprising polyethylene glycol (PEG) blocks and hydrophobic polymer blocks. The peptide ligand consists of an amino acid sequence wherein at least one pair of amino acids are of an opposite charge, the members of said pair are separated by a spacer consisting of 1-12 amino acid residues comprising at least one hydrophobic amino acid, and the length of said amino acid sequence is greater than 5 and less than 20 amino acids. Each peptide ligand is attached to said nanoparticle through conjugation to a block copolymer of said nanoparticle by covalent bonding to a PEG block. The conjugate has an average diameter between about 1 and about 700 nm.

In one embodiment, the hydrophobic polymer is selected from the group consisting of poly(lactic acid), poly(lactic acid-co-glycolic acid), polycaprolactone, polyanhydrides, polyorthoesters, polyamides, polycarbonates, polyalkylenes, poly-alkylene terepthalates, polyvinyl halides, polysiloxanes, poly(vinyl acetate), polystyrene, polyurethanes, synthetic celluloses, polyacrylic acids, poly(butyric acid), poly (valeric acid), poly(lactide-co-capro-lactone) and combinations thereof.

In another embodiment, the conjugate has an average diameter of equal to or greater than about 500 nm.

In an alternative embodiment, the conjugate has an average diameter of between about 50-500 nm. In a further embodiment, the conjugate further comprises a targeting agent selected from the group consisting of RGD peptide, EGF peptide, DV3 peptide, an LYP peptide, a membrane-binding domain of IGFBP3, fMLF, mannose, transferrin ligand, monoclonal anti-bodies, and drug conjugated derivatives thereof.

In an alternative embodiment, the conjugate has an average diameter of smaller than about 10 nm. In a further embodiment, the conjugate comprises a targeting agent selected from the group consisting of RGD peptide, EGF peptide, DV3 peptide, an LYP peptide, a membrane-binding domain of IGFBP3, fMLF, mannose, transferrin ligand, monoclonal anti-bodies, and drug conjugated derivatives thereof.

In a further embodiment, the peptide ligand is bound to the nanoparticle via a linkage selected from the group consisting of an amide, a thio ether, a 1,2,3-triazole.

In a further embodiment, the peptide ligand comprises a monodisperse PEG block, wherein the monodisperse PEG block bound to the nanoparticle via a linkage selected from the group consisting of an amide, a thio ether, a 1,2,3-triazole. Other suitable linkages include for example ether, ester, carbamate, and amine.

In a further embodiment, the amino acid sequence is at least 75% identical to SEQ ID NO: 4, and wherein further, non-identical amino acids are conservative substitutions of corresponding residues of SEQ ID NO: 4. In an alternative embodiment, the amino acid sequence is at least 75% identical to SEQ ID NO: 5, and wherein further, non-identical amino acids are conservative substitutions of corresponding residues of SEQ ID NO: 5. In an alternative embodiment, the amino acid sequence is at least 75% identical to SEQ ID NO: 6, and wherein further, non-identical amino acids are conservative substitutions of corresponding residues of SEQ ID NO: 6.

In a further embodiment, the therapeutic agent is a pharmaceutical active, diagnostic, biologic, imaging or targeting agent.

Another aspect of the invention provides a composition including the above conjugate and a pharmaceutically acceptable carrier.

In one embodiment, the therapeutic agent in the composition is a pharmaceutical active, diagnostic, biologic, imaging or targeting agent.

In one embodiment, the conjugate of the composition has an average diameter of between about 50-500 nm and said composition further comprises a fat or oil.

In another embodiment, the composition includes a stabilizer selected from vitamin E, fat, wax, and oil.

In another embodiment, the pharmaceutical active agent of the composition is selected from the group consisting of tetracyclines, rifamycins, macrolides, penicillins, cephalosporins, beta-lactam antibiotics, aminoglycosides, chloramphenicol, sulfamethoxazole, vancomycin, ciprofloxacin, fusidic acid, trimethoprim, metronidazole, clindamycin, mupirocin, amphotericinB, fluconazole, sulbactam, minocycline, rifampin, erythromycin, nafcillin, cefazolin, imipenem, aztreonam, gentamicin, sulfamethoxazole, vancomycin, ciprofloxacin, trimethoprim, metronidazole, clindamycin, teicoplanin, mupirocin, azithromycin, clarithromycin, ofloxacin, lomefloxacin, norfloxacin, nalidixic acid, sparfloxacin, pefloxacin, amifloxacin, enoxacin, fleroxacin, temafloxacin, tosufloxacin, clinafloxacin, sulbactam, clavulanic acid, amphotericin B, fluconazole, itraconazole, ketoconazole, nystatin, acyclovir, acyclovir prodrugs, famcyclovir, zidovudine, didanosine, stavudine, lamivudine, zalcitabine, n-docosanol, tromantadine, idoxuridine, amorolfine, isoconazole, clotrimazole, econazole, miconazole, nystatin, terbinafine, bifonazole, amphotericin, griseofulvin, keto-conazole, fluconazole, flucytosine, fezatione, ticlatone, tolnaftate, triacetin, zinc pyrithione, sodium pyrithione, steroidal anti-inflammatory compounds, ibuprofen, flurbiprofen, ketoprofen, aclofenac, diclofenac, aloxiprin, aproxen, diflunisal, fenoprofen, indomethacin, mefenamic acid, naproxen, phenylbutazone, piroxicam, salicylamide, salicylic acid, sulindac, desoxysulindac, tenoxicam, tramadol, ketoralac, flufenisal, salsalate, triethanolamine salicylate, aminopyrine, antipyrine, oxyphenbutazone, apazone, cintazone, flufenamic acid, clonixerl, clonixin, meclofenamic acid, flunixin, coichicine, demecolcine, allopurinol, oxypurinol, benzydamine hydrochloride, dimefadane, indoxole, intrazole, mimbane hydrochloride, paranylene hydrochloride, tetrydamine, benzindopyrine hydrochloride, fluprofen, ibufenac, naproxol, fenbufen, cinchophen, diflumidone sodium, fenamole, flutiazin, metazamide, letimide hydrochloride, nexeridine hydrochloride, octazamide, molinazole, neocinchophen, nimazole, proxazole citrate, tesicam, tesimide, tolmetin, triflumidate, sancycline, sancycline analogs, olvanil, olvanil analogs, retro-olvanil, retro-olvanil analogs, olvanil carbamate, budesonide, budesonide analogs, methylprednisolone, methylprednisolone analogs, dexamethasone, dexamethasone analogs, camptothecin, carboplatin, doxorubicin, paclitaxel, saquinavir mesylate, amprenavir, ritonavir, indinavir, nelfinavir mesylate, tipranavir, rilpivirine, dolutegravir, ciclopirox, darunavir and atazanavir sulfate.

Another aspect of the invention provides a method for the gastrointestinal delivery of a therapeutic agent with poor gastrointestinal absorption to a patient in need thereof, comprising administering to said patient a composition according of the present invention by oral administration.

Another aspect of the invention provides a peptide ligand comprising an amino acid sequence wherein at least one pair of amino acids are of an opposite charge, the members of said pair are separated by a spacer consisting of 1-12 amino acid residues comprising at least one hydrophobic amino acid, the length of said amino acid sequence is greater than 5 and less than 20 amino acids, and said peptide ligand is bound to a monodisperse PEG block.

In one embodiment, the first member of said pair of amino acids of said amino acid sequence is selected from the group consisting of D and E, and said second member of opposite charge is independently selected from the group consisting of K, R, and H. In an alternative embodiment, the amino acid sequence comprises two pairs of amino acids of opposite polarity.

In another embodiment, the amino acid sequence is at least 75% identical to SEQ ID NO: 4, and wherein further, non-identical amino acids are conservative substitutions of corresponding residues of SEQ ID NO: 4. In an alternative embodiment, the amino acid sequence is at least 75% identical to SEQ ID NO: 5, and wherein further, non-identical amino acids are conservative substitutions of corresponding residues of SEQ ID NO: 5. In an alternative embodiment, the amino acid sequence is at least 75% identical to SEQ ID NO: 6, and wherein further, non-identical amino acids are conservative substitutions of corresponding residues of SEQ ID NO: 6.

In another embodiment, the monodisperse PEG unit has a molecular weight of less than about 500.

Another aspect of the present invention provides an amino acid sequence at least 75% identical to SEQ ID NO: 6, wherein further, non-identical amino acids are conservative substitutions of corresponding residues of SEQ ID NO: 6.

Additional embodiments and advantages to the instant invention will be readily apparent to one of skill in the art, based on the disclosure provided herein.

DETAILED DESCRIPTION OF THE INVENTION

1. Overview

Figure 1:
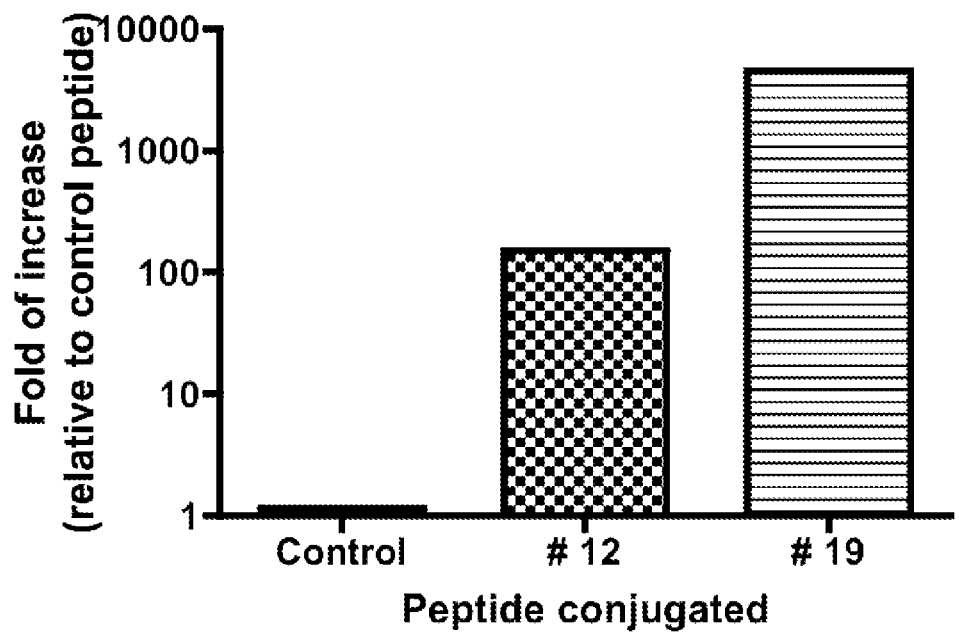
FIG. 1. Compares the translocation efficiency of peptides #12 (SEQ ID NO. 2) and #19 (SEQ ID NO. 1) with controls.

The instant invention relates to the discovery of peptide ligands that can be used to transport active agents that are otherwise poorly absorbed gastrointestinally (e.g. macromolecular drugs and/or small molecules or other therapeutically useful compounds) across the intestinal epithelial cell barrier in a chylomicron-forming lipid-dependent manner. The identified peptide ligands can be bound to a carrier and/or a therapeutic agent.

2. Definitions

As used herein, the singular forms "a," "an" and "the" include plural references unless the content clearly dictates otherwise.

The term "about", as used here, refers to +/−10% of a value.

The term "amino acid" refers to natural and/or unnatural or synthetic amino acids, including glycine and both the D and L optical isomers, amino acid analogs (for example norleucine is an analog of leucine) and peptidomimetics.

As used herein "conservative substitutions" refers to changes that can generally be made to an amino acid sequence without altering activity, an amino acid belonging to a grouping of amino acids having a particular size or characteristic can be substituted for another amino acid. Substitutes for an amino acid sequence may be selected from other members of the class to which the amino acid belongs. For example, the nonpolar (hydrophobic) amino acids include alanine, leucine, isoleucine, valine, proline, phenylalanine, tryptophan, and tyrosine. The polar neutral amino acids include glycine, serine, threonine, cysteine, tyrosine, asparagine and glutamine. The positively charged (basic) amino acids include arginine, lysine and histidine. The negatively charged (acidic) amino acids include aspartic acid and glutamic acid. Exemplary conservative substitutions include, but are not limited to, Lys for Arg and vice versa to maintain a positive charge; Glu for Asp and vice versa to maintain a negative charge.

The term "hydrophobic" refers to a substance, molecule, or a domain of a substance of molecule that does not dissolve or is not wetted by water. The energetic interaction between a hydrophobic substance, molecule, or domain is unfavorable. Examples include solvents such as hydrocarbons and esters that when mixed with water undergo phase separation.

The term "hydrophilic" refers to a property wherein a substance, a molecule, or a domain of a substance or molecule has an affinity for water or aqueous fluids. A hydrophilic substance, molecule, or domain can dissolve, become deliquescent, or be wetted by water or the aqueous substance. A substance, molecule, or a domain thereof is hydrophilic when the energetics of the interaction between the substance, molecule, or domain and water or an aqueous fluid is favorable.

As used herein, a "spacing group" or "spacer sequence" refers to a portion of a chemical structure, which connects two or more substructures such as amino acids, labels, polymers, through a functional group. For example a spacer sequence may be an amino acid sequence consisting of at least 2 amino acids. The atoms of a spacing group and the atoms of a chain within the spacing group are themselves connected by chemical bonds.

As used herein, the term "linker" refers to a chemical moiety that connects a molecule to another molecule, covalently links separate parts of a molecule or separate molecules. The linker provides spacing between the two molecules or moieties such that they are able to function in their intended manner. Examples of linking groups include peptide linkers, enzyme sensitive peptide linkers/linkers, self-immolative linkers, acid sensitive linkers, multifunctional organic linking agents, bifunctional inorganic crosslinking agents and other linkers known in the art. The linker may be stable or degradable/cleavable.

As used herein the term "therapeutic agent" encompasses pharmaceutically active therapeutic agents, diagnostic, biologic and targeting agents, as well as adjuvants.

As used herein, the term "diagnostic agent" refers to any molecule which produces, or can be induced to produce, a detectable signal. The diagnostic agent may be any diagnostically useful compound that may be bound via a functional group thereon to the composition of the invention. Diagnostic moieties having reporter molecules that can be detected by imaging equipment may include radioactive, paramagnetic, fluorescent or radioopaque chemical entities. Non-limiting examples of labels include radioactive isotopes, enzymes, enzyme fragments, enzyme substrates, enzyme inhibitors, coenzymes, catalysts, fluorophores, dyes, chemiluminescers, luminescers, or sensitizers; a non-magnetic or magnetic particle, iodinated sugars that are used as radioopaque agents, and can be appended to linker backbones using ester or other linkages.

As used herein, the term "biologic agent" encompasses substances generally derived from a biological source, such as from an organism, a cell line, an isolated tissue, or the like which includes proteins, peptides, carbohydrates, polysaccharides, nucleic acid molecules, examples include antibodies and fragments thereof (including humanized, single chain, chimeric antibodies, fab regions, fc regions, complementarity determining regions, and any combination thereof), peptides (including hormones, for example insulin), and nucleic acid molecules (including DNA, RNAs, microRNAs, siRNAs, shRNAs, tRNAs, antisense, aptamers, ribozymes, external guide sequences for ribonuclease P, and triplex forming agents).

As used herein the term "nucleic acid" refers to a molecular entity composed of a nucleobase, sugar moiety, and phosphate group, or analogs thereof. Examples include the DNA nucleotides, i.e., adenine, guanine, cytosine, and thymidine, or the RNA nucleotide uracil, or synthetic analogs thereof. Examples of sugar moieties to which the nucleobases are covalently bonded include but are not limited to ribose and deoxyribose. Analogs of sugars can also be present; for example, halodeoxyribose analogs.

As used herein the term "peptide" is used interchangeably with the term "protein" and "amino acid sequence", in its broadest sense refers to a compound of two or more subunit amino acids, amino acid analogs or peptidomimetics.

As used herein, the term "amino acid" refers to natural and/or unnatural or synthetic amino acids, including glycine and both the D and L optical isomers, amino acid analogs (for example norleucine is an analog of leucine) and peptidomimetics.

As used herein, the term "conservative substitution" refers to a change that can generally be made to an amino acid sequence without altering activity, an amino acid belonging to a grouping of amino acids having a particular size or characteristic can be substituted for another amino acid. Substitutes for an amino acid sequence may be selected from other members of the class to which the amino acid belongs. For example, the nonpolar (hydrophobic) amino acids include alanine, leucine, isoleucine, valine, proline, phenylalanine, tryptophan, and tyrosine. The polar neutral amino acids include glycine, serine, threonine, cysteine, tyrosine, asparagine and glutamine. The positively charged (basic) amino acids include arginine, lysine and histidine. The negatively charged (acidic) amino acids include aspartic acid and glutamic acid. Exemplary conservative substitutions include, but are not limited to, Lys for Arg and vice versa to maintain a positive charge; Glu for Asp and vice versa to maintain a negative charge.

"Identical" or "identity" as well as "homology" or "homologue" as used herein in the context of two or more nucleic acids or peptide sequences, means that the sequences have a specified percentage of nucleotides or amino acids that are the same over a specified region. The percentage may be calculated by comparing optimally aligning the two sequences, comparing the two sequences over the specified region, determining the number of positions at which the identical residue occurs in both sequences to yield the number of matched positions, dividing the number of matched positions by the total number of positions in the specified region, and multiplying the result by 100 to yield the percentage of sequence identity. In cases where the two sequences are of different lengths or the alignment produces staggered end and the specified region of comparison includes only a single sequence, the residues of single sequence are included in the denominator but not the numerator of the calculation. When comparing DNA and RNA, thymine (T) and uracil (U) are considered equivalent. Identity may be performed manually or by using computer sequence algorithm such as BLAST or BLAST 2.0.

"Substantially identical" as used herein refers to that a first and second sequence are at least 60%, 65%, 70%, 75%, 80%, 85%, 90%, 95%, 97%, 98% or 99% identical over a region of 8, 9, 10, 11, 12, 13, 14, 15, 16, 17, 18, 19, 20, 21, 22, 23, 24, 25, 30, 35, 40, 45, 50 or more nucleotides or amino acids, or with respect to nucleic acids, if the first sequence is substantially complementary to the complement of the second sequence. Preferably, such variant nucleic acid and peptide sequences will share 75% or more (i.e. 80, 85, 90, 95, 97, 98, 99% or more) sequence identity with the sequences recited in the application. Preferably such sequence identity is calculated with regard to the full length of the reference sequence (i.e. the sequence recited in the application).

"Substantially complementary" as used herein refers to that a first sequence is at least 60%, 65%, 70%, 75%, 80%, 85%, 90%, 95%, 97%, 98% or 99% identical to the complement of a second sequence over a region of 8, 9, 10, 11, 12, 13, 14, 15, 16, 17, 18, 19, 20, 21, 22, 23, 24, 25, 30, 35, 40, 45, 50 or more nucleotides, or that the two sequences hybridize under stringent hybridization conditions.

As used herein, "targeting agents" refer to ligands, polymers, proteins, cytokines, chemokines, peptides, nucleic acids, lipids, saccharides or polysaccharides, small molecules or any combination thereof, (for example a gylcolipid, glycoprotein etc) that bind to a receptor or other molecule on the surface of a targeted cell. An exemplary small-molecule targeting compound is folate, which targets the folate receptor. These targeting agents may be in addition to the peptide sequences disclosed that facilitate transport across the intestinal epithelium. The degree of specificity can be modulated through the selection of the targeting molecule. For example, antibodies are very specific. These can be polyclonal, monoclonal, fragments, recombinant, or single chain, many of which are commercially available or readily obtained using standard techniques.

Additional examples of targeting agents include RGD peptide, EGF peptide, DV3 (LGASWHRPDKC) peptide, a LYP peptide (CGNKRTRGC), a membrane-binding domain of IGFBP3 (QCRPSKGRKRGFCW), fMLF, mannose, transferrin ligand and monoclonal anti-bodies, including the drug conjugated derivatives of the above mentioned agents.

As used herein, the term "carrier" can be a liquid phase carrier or a solid phase carrier, e.g., gel, nanoparticle, microparticle, delivery vehicle, a phage or a virion. A carrier may be further modified by attachment of one or more different molecules, such as additional targeting and/or attachment molecules, and/or therapeutic, diagnostic, targeting or biologic agents. The agents may be incorporated into, onto, or coupled to a carrier.

As used herein, the term "nanoparticle" (NP) refers to a structure having at least one dimension between about 1-1,000 nm in one or more dimensions. Exemplary nanoparticles include but are not limited to dendrimers, liposomes, semiconductor crystals (e.g., quantum dots), metal particles, magnetic particles, carbon tubes, Bucky balls, quantum rods (QRs), quantum wires (QWs), and other nanoparticles.

As used herein, the term "liposome" refers to a lipid vesicle composed of concentric phospholipid bilayers which enclose an aqueous interior (Gregoriadis, et al., hit J Pharm 300, 125-30 2005; Gregoriadis and Ryman, Biochem J 124, 58P (1971)). The lipid vesicles comprise either one or several aqueous compartments delineated by either one (unilamellar) or several (multilamellar) phospholipid bilayers (Sapra, et al., Curr Drug Deliv 2, 369-81 (2005)).

As used herein, the term "dendrimer" encompasses polymers distinguished by their repeated branching structure emanating from a central core.

As used herein, a "microparticle" (MP) refers to a particle having an average diameter on the order of micrometers (i.e., between about 1 micrometer and about 1 mm), while a "nanoparticle" is a particle having an average diameter on the order of nanometers (i.e., between about 1 nm and about 1 micrometer. The particles may be spherical or non-spherical, in some cases. Nanoparticles and microparticles are jointly referred to herein as particles unless otherwise specified.

As used herein, the terms "polymer," "polymeric" and similar terms have the usual meaning known to those skilled in the art and thus may be used to refer to homopolymers, copolymers (e.g., random copolymer, alternating copolymer, block copolymer, graft copolymer) and mixtures thereof.

As used herein, the term "block copolymer" refers to a polymer composed of two or more different chemical types of monomer units, wherein monomer units of one type are largely associated only with each other in particular domains, "blocks," of the polymer and monomer units of another type are also largely associated only with each other in other particular domains or blocks of the polymer. The backbone or continuous molecular chain of the polymer contains domains of at least two blocks.

As used herein, "PEG" is used herein as an abbreviation for polyethylene glycol. PEGs are included within the broader class of polyalkylene oxides, which include PEG as well as polypropylene glycols, and polyglycol copolymers. PEG can have a range of molecular weights. The PEG molecular weight range contemplated for use in the present invention is from about 1000 to about 100,000 Da. PEG can be linear, branched, multi-arm, or a combination of branched and multi-arm. Various PEGs can be derivatized with various groups, such as activated ester (N-hydroxy succinimidy ester, for example), p-nitrophenyl, aldehyde, amine, thiol, activated thiol (thiopyridine activated thiol, for example), vinyl sulfone, maleimide, aminooxy, hydrazine, tosyl, azide, alkyne, cyclooctyne and idoacetamide.

As used herein, "intestinal epithelial barrier" refers to eptithelial cells that line the intestine of an animal. An intestinal eptithelial barrier can be provided in vitro or in situ, or is located within the intestines of an animal. A non-limiting example of an intestinal epithelial barrier in vitro is a monolayer of Caco-2 cells in a solid support such as a petri dish.

"Animal" includes all vertebrate animals including humans. In particular, the term "vertebrate animal" includes, but not limited to, mammals, humans, canines (e.g., dogs), felines (e.g., cats); equines (e.g., horses), bovines (e.g., cattle), porcine (e.g., pigs), mice, rabbits, goats, as well as in avians. The term "avian" refers to any species or subspecies of the taxonomic class ava, such as, but not limited to, chickens (breeders, broilers and layers), turkeys, ducks, a goose, a quail, pheasants, parrots, finches, hawks, crows and ratites including ostrich, emu and cassowary.

3. Peptide Ligands

The present invention provides peptide ligands. The peptide ligands of the instant invention include an amino acid sequence of 5-20 amino acids. Such sequences include at least one pair of amino acids of opposite charge, which are separated by an amino acid spacer of 1-12 amino acid residues containing at least one hydrophobic amino acid. For example, in one embodiment, the first member of the pair of amino acids is negatively charged. Such amino acids include, but are not limited to, aspartic acid (D) or glutamic acid (E). The second member of the pair of amino acids is positively charged. Such amino acids include, but are not limited to, lysine (K), arginine (R), or histidine (II). The spacer element includes at least one hydrophobic amino acid, which includes, but is not limited to, alanine (A), isoleucine (I), leucine (L), methionine (M), phenylalanine (F), tryptophan (W), tyrosine (Y), valine (V), and combinations thereof.

The peptide ligand sequences of the instant invention also may include multiple pairs of oppositely charged amino acids separated by a single or multiple spacers containing one or more hydrophobic amino acids or amino acid sequences. To this end, such multiple pairs may be provided in juxtaposition or in a nested relationship. In some embodiments, the peptide ligands of the instant invention include an amino acid sequence of 5, 6, 7, 8, 9, 10, 11, 12, 13, 14, 15, 16, 17, 18, 19, or 20 amino acids. Such sequences include at least one pair of amino acids of opposite charge, which are separated by an amino acid spacer of 1, 2, 3, 4, 5, 6, 7, 8, 9, 10, 11, or 12 amino acid residues containing at least one hydrophobic amino acid.

In certain non-limiting embodiments, the pair(s) of oppositely charged amino acids are flanked with one or more non-charged or hydrophobic amino acids or sequences of non-charged amino acids, hydrophobic amino acids or a combinations thereof. Such amino acids may be provided at the N-terminus and/or C-terminus of the oppositely charged amino acid pair or the peptide ligand sequence. Examples of non-charged amino acids include, but are not limited to, serine (S), threonine (T), asparagine (N), glutamine (Q) and, in certain instances, cysteine (C), glycine (G), and proline (P) valine (V), isoleucine (I), leucine (L), tryptophan (W) and proline (P). Hydrophobic amino acids may be any amino acid as defined herein. In other related embodiments, the described invention provides amino acid variants of the identified ligand peptide sequences, SEQ ID NOs: 1-6. These amino acid variants have at least 70%, at least 75%, at least 80%, at least 85%, at least 90%, at least 95%, at least 96%, at least 97%, at least 98%, or at least 99%, or greater, sequence identity compared to a amino acid sequence of this invention, as determined using the methods described herein, (for example, BLAST analysis using standard parameters). One skilled in this art will recognize that these values can be appropriately adjusted to determine corresponding identity of proteins encoded by two nucleotide sequences by taking into account codon degeneracy, amino acid similarity, reading frame positioning, and the like. In other related embodiments, the described invention includes the following formulas, Formulas 1-5, for amino acid variants of the identified ligand peptide sequences.

A. Formula 1

An embodiment of the present invention may be represented by the following Formula 1:

$$X_1B_1Z_1Z_2Z_3B_2X_2,$$

wherein $X_1$-$X_2$ are not charged or hydrophobic amino acids, $Z_1$-$Z_3$ is a spacer sequence of at least one hydrophobic amino acid, and $B_1$ and $B_2$ are members of said at least one pair and have opposite charge.

A non-limiting example of such an amino acid sequence includes, but is not limited to, TKWPVD (SEQ ID NO: 4). The peptide ligands of the instant invention may also include variants or homologues of SEQ ID NO: 4, which may be at least 75% identical to SEQ ID NO: 1 or which may contain conservative substitutions of corresponding amino acid residues.

B. Formula 2

An embodiment of the present invention may be represented by the following Formula 2:

$$X_1B_1Z_1Z_2Z_3B_2X_2X_3X_4,$$

wherein $X_1$-$X_4$ are not charged or hydrophobic amino acids, $Z_1$-$Z_3$ is a spacer sequence of at least one hydrophobic amino acid, and $B_1$ and $B_2$ are members of said at least one pair and have opposite charge.

A non-limiting example of such an amino acid sequence includes, but is not limited to, TKWPVDMCP (SEQ ID NO: 5). The peptide ligands of the instant invention may also include variants or homologues of SEQ ID NO: 4, which may be at least 75% identical to SEQ ID NO: 1 or which may contain conservative substitutions of corresponding amino acid residues.

C. Formula 3

An embodiment of the present invention may be represented by the following Formula 3:

$$X_1B_1Z_1Z_2Z_3B_2X_2X_3X_4X_5X_6X_7,$$

wherein $X_1$-$X_7$ are not charged or hydrophobic amino acids, $Z_1$-$Z_3$ is a spacer sequence of at least one hydrophobic amino acid, and $B_1$ and $B_2$ are members of said at least one pair and have opposite charge.

A non-limiting example of such an amino acid sequence includes, but is not limited to, TKWPVDMCPNVS (SEQ ID NO: 1). The peptide ligands of the instant invention may also include variants or homologues of SEQ ID NO: 1, which may be at least 75% identical to SEQ ID NO: 1 or which may contain conservative substitutions of corresponding amino acid residues.

Another example of such an amino acid sequence is TKWPVDN/eSPNVS (SEQ ID. NO. 6). In comparison with SEQ ID. NO. 1, replacement of the oxidation-prone amino acids (methionine and cysteine) with their biosteric counterparts (norleucine and serine respectively) in SEQ ID. NO. 6 led to better solubility and less undesirable aggregation. The peptide ligands of the instant invention also include variants or homologues of SEQ ID NO: 6, which may be at least 75% identical to SEQ ID NO: 6 or which may contain conservative substitutions of corresponding amino acid residues.

The salt-bridge in SEQ ID. NO. 6 attributable to the presence of the pair of oppositely charged amino acids is important. The importance of the salt-bridge appears to be explained by the amphiphilic conformation maintained by the salt-bridge that seems to allow the resulting conjugates or particles to be associated with, or incorporated into, lipid micelle(s).

D. Formula 4

An embodiment of the present invention may be represented by the following Formula 4:

$$X_1B_1B_2Z_1Z_2Z_3Z_4Z_5B_3Z_6Z_7B_4,$$

wherein $X_1$ is either an uncharged amino acid or hydrophobic amino acid, $Z_1$-$Z_7$ is a spacer sequence of at least one hydrophobic amino acid, and $B_1$-$B_4$ are charged amino acids and wherein $B_1$ and $B_2$ have an identical charge which charge is opposite to the charge of $B_3$ and $B_4$.

A non-limiting example of such an amino acid sequence includes, but is not limited to, QDDVQTWQRQPK (SEQ ID NO: 2). The peptide ligands of the instant invention may also include variants or homologues of SEQ ID NO: 2, which may be at least 75% identical to SEQ ID NO: 2 or which may contain conservative substitutions of corresponding amino acid residues.

E. Formula 5

An embodiment of the present invention may be represented by the following Formula 5:

$$X_1B_1Z_1Z_2B_2Z_3B_3Z_4B_4Z_5Z_6B_5Z_7B_6X_2X_3X_4,$$

wherein $X_1$-$X_4$ represent uncharged or hydrophobic amino acids and $Z_1$-$Z_7$ represent the spacer sequence of at least one hydrophobic amino acid. $B_1$-$B_6$ represent charged amino acids, wherein $B_1$, $B_2$ and $B_3$ have an identical charge that is opposite to that of $B_4$, $B_5$ and $B_6$.

A non-limiting example of such an amino acid sequence includes, but is not limited to, GENFEQDWKSLRPHSSN (SEQ ID NO: 3). The peptide ligands of the instant invention may also include variants or homologues of SEQ ID NO: 3, which may be at least 75% identical to SEQ ID NO: 3 or which may contain conservative substitutions of corresponding amino acid residues.

The peptide ligand of the present invention may further include a monodisperse PEG block, which is bound to the amino acid sequence. Attachment of such a PEG block enhances steric exposure of the functional group for the conjugation with a block copolymer as well as to prevent aggregation during the post-assembly process. Suitable monodisperse PEG block embodiments have MW below about 1200, below about 1000, below about 900, below about 800, below about 700, below about 600, below about 500, or below about 400.

4. Compositions/Conjugates

The present invention provides a composition comprising a peptide ligand of the present invention, and a therapeutic agent or a carrier. The peptide ligands can be bound to a carrier or conjugated to at least one therapeutic, biologic, diagnostic or target agent to transport the carrier or conjugate across the intestinal epithelium barrier. One with ordinary skill in the art will understand how to directly conjugate the peptide ligands to a therapeutic agent or carrier, or utilize a linker to bind the peptide ligand to a therapeutic agent or carrier. One or more peptide ligands, as well as different variants of peptide ligands may be bound to the agent or carrier.

In a further embodiment the invention provides a composition comprising an amino acid sequence of the invention and a therapeutic agent bound to the same carrier molecule. In related embodiments, multiple agents, as well as multiple types of agents may be conjugated to the peptide ligand or to the carrier. Also, multiple peptide ligands, and variant peptide ligands may be bound to the agent and carrier and all ligands and agents may be bound to a common carrier.

In a further embodiment the invention provides a conjugate comprising a peptide ligand as described above and a nanoparticle carrier. The nanoparticle includes a hydrophobic therapeutic agent admixed with a biocompatible block copolymer. The biocompatible block copolymer contains polyethylene glycol (PEG) blocks and hydrophobic polymer blocks. Each peptide ligand is conjugated to the block copolymer by covalent bonding to a PEG block. In some embodiments, the conjugate of the present invention has a hydrodynamic radii between about 25 and about 100 nm, corresponding to a diameter between about 50 and about 200 nm. Other exemplary ranges for the diameters include between about 1 and about 700 nm, between about 5 and about 700 nm, between about 10 and about 700 nm, between about 1 nm and about 700 nm, between about 5 nm and about 600 nm, between about 5 nm and about 500 nm, between about 10 nm and about 500 nm, between about 10 nm and about 400 nm, between about 10 nm and about 300 nm, between about 20 nm and about 500 nm, between about 20 nm and about 400 nm, between about 20 nm and about 300 nm, between about 50 nm and about 500 nm, between about 50 nm and about 400 nm, between about 50 nm and about 300 nm, between about 50 nm and about 200 nm, between about 50 nm and about 150 nm, between about 80 nm and about 500 nm, between about 80 nm and about 400 nm, between about 80 nm and about 300 nm, between about 80 nm and about 300 nm, between about 80 nm and about 200 nm, between about 80 nm and about 150 nm, and between about 80 nm and about 100 nm.

The hydrodynamic size of the conjugate determines whether, after administration, systemic or lymphatic delivery will occur in the small intestine, or the conjugate particles will lodge in intestinal tissue. Gut blood capillary pore size is smaller than gut lymphatic capillary pore size. Conjugates smaller than the gut blood capillary pores will be predominantly delivered systemically. Conjugates larger than the gut blood capillary pore size but smaller than gut lymphatic capillary pore size will be predominantly delivered lymphatically. Conjugates larger than gut lymphatic capillary pore size will lodge in intestinal tissues.

Accordingly, by designing and manipulating the hydrodynamic size of the conjugate, different pathways of delivery can be accomplished. For example, chylomicrons (CMs) are not absorbed directly into blood stream because they are greater than the gut blood capillary pore size but fit into the gaps of the gut lymphatic capillaries, which are up to one micron in size. Therefore, the conjugate particles of the present invention can be tuned in CM size to enter the gut lympatics, or tuned in size greater than CM to linger in the gut lamina propria for a considerable time, leading to sustained drug release into blood circulation. Such concepts find applications in the delivery of therapeutic agents including HIV-1 drugs because gut lamina propria plays a critical role in HIV-1 disease and viral persistence. Biologics (e.g. insulin and other peptides) susceptible to enzymes attack or fast clearance in circulation can also be delivered in a sustained release manner by conjugates of suitable size, which can be retained outside the blood circulation for a desirable period of time.

Conjugates designed to lodge in intestinal tissue have an average diameter of equal or greater than about 500 nm. Other non-limiting examples of suitable average diameters for the conjugate include equal or greater than about 250 nm, equal or greater than about 300 nm, equal or greater than about 350 nm, equal or greater than about 400 nm, equal or greater than about 450 nm, equal or greater than about 550 nm, equal or greater than about 600 nm, equal or greater than about 700 nm, equal or greater than about 800 nm, equal or greater than about 900 nm, and equal or greater than about 1000 nm. In some embodiments, substantially all of the conjugate particles have the above suitable average diameter. In other non-limiting exemplary embodiments, more than about 95%, about 90%, about 85%, about 80%, about 75%, about 70%, about 65%, about 60%, about 55%, or about 50% of the conjugate particles have the above suitable average diameter.

Conjugates designed for delivery for gut lymphatic capillary have an average diameter of between about 100-500 nm. Other non-limiting examples of suitable range of diameters for the conjugate include between about 50-100 nm, between about 50-150 nm, between about 50-200 nm, between about 50-250 nm, between about 80-100 nm, between about 80-150 nm, between about 80-200 nm, between about 100-150 nm, between about 100-200 nm, between about 150-250 nm, between about 200-300 nm, between about 300-400 nm, between about 400-500 nm, between about 500-600 nm. In some embodiments, substantially all of the conjugate particles have a diameter within the suitable range of diameters. In other non-limiting exemplary embodiments, more than about 95%, more than about 90%, more than about 85%, more than about 80%, more than about 75%, more than about 70%, more than about 65%, more than about 60%, more than about 55%, or more than about 50% of the conjugate particles have a diameter within the above suitable range.

Conjugates designed for delivery through gut blood capillary have an average diameter of smaller than about 200 nm. Other non-limiting examples of suitable average diameters for the conjugate include smaller than about 150 nm, smaller than about 100 nm, smaller than about 50 nm, smaller than about 40 nm, smaller than about 30 nm, smaller than about 20 nm, smaller than about 10 nm, smaller than about 9 nm, smaller than about 8 nm, smaller than about 7 nm, smaller than about 6 nm, smaller than about 5 nm, smaller than about 4 nm, smaller than about 3 nm, smaller than about 2 nm, and smaller than about 1 nm. In some embodiments, substantially all of the conjugate particles have a diameter of the above the suitable average diameter. In other non-limiting exemplary embodiments, more than about 95%, more than about 90%, more than about 85%, more than about 80%, more than about 75%, more than about 70%, more than about 65%, more than about 60%, more than about 55%, or more than about 50% of the conjugate particles have the above suitable average diameter.

In a further embodiment, conjugates for lymphatic and blood delivery further comprise a receptor targeting agent including for example RGD peptide, EGF peptide, DV3 (LGASWHRPDKC) peptide, a LYP peptide (CGNKRTRGC), a membrane-binding domain of IGFBP3 (QCRPSKGRKRGFCW), fMLF, mannose, transferrin ligand, monoclonal antibodies, and drug conjugated derivatives of thereof.

The peptide ligand can be bound to the PEG block by various chemical linkage including for example, an amide, a thio ether, an ether, a disulfide, a carbamate, an ester, a 1,2,3-triazole, dihydropyridizine or a tautomer thereof. In some embodiments, the linkage is an amide, a thio ether, a 1,2,3-triazole, dihydropyridizine or a tautomer thereof.

Procedures for forming such linkages are well known in the art. For example, an amide linkage can be formed by activating a carboxylic acid with NHS (N-hydroxysuccinate) and reacting the activated acid with an amine. Copper-catalyzed or copper-free click chemistry may also be employed to conjugate the peptide ligand and the nanoparticle carrier and result in a triazole based linkage. Exemplary linkage formation is shown in Table 1.

TABLE 1

Chemical options for NP-ligand conjugations

| Reaction type | Linkage formed | Reactant A | Reactant B | Polymer or NP surface | Ligand |
|---|---|---|---|---|---|
| Maleimide - thiol | Thio ether | Maleimide | —SH | A | B |
| Amidation | Amide | $NH_2$ | COOH* | A, B | A, B |
| Click-chemistry - Catalyst free | 1,2,3-triazole derivatives | azide | Strained alkynes | A, B | A, B |
| Click-chemistry - Cu(I) catalyzed | 1,2,3-triazole | azide | akynnes | A, B | A, B |

*Activated carboxyl functional group. In aqueous medium for post-assembly NHS (N-hydroxysuccinate) in organic solvents for pre-assembly any peptide coupling reagents applicable Different methods can be utilized to functionalize the polymer chains with peptide ligands, including the pre- and the post-assembly approaches. In the pre-assembly method the hydrophilic end of the diblock co-polymer is covalently attached to the ligand that carries a suitable functional group for conjugation. In the case of post-assembly approach the drug loaded NPs are to be conjugated to the ligands. Regardless of the conjugation strategy, the resulting conjugate should be able to present most of the biochemical characteristics of the peptide ligand (e.g. receptor binding functions, lipid interactions). The new chemical bonds formed during conjugation should be stable in the GI tract, lymphatics and circulation for days (e.g. 1-3 or longer) to facilitate the preferable daily oral administration.

In some embodiments, the peptide ligand of the conjugate comprises a monodisperse PEG block, which is as described above. In some embodiments, the peptide ligand of the conjugate comprises an isolated amino acid sequence, which is at least 75% identical to SEQ ID NO: 6, and wherein further, non-identical amino acids are conservative substitutions of corresponding residues of SEQ ID NO: 6.

A. Carrier

The carrier may be formed of any suitable pharmaceutically acceptable or therapeutically acceptable material, which are well known. The carrier may comprise of a metal, glass, lipid, protein, polymer or any combinations thereof. In a preferred embodiment the carrier is a particle formed from biocompatible or biodegradable polymers such as polylactic and/or polyglycolic acids, polyanhydrides, polycaprolactones, polyethylene oxides, polybutylene terephthalates, starches, cellulose, chitosan, and/or combinations of these. The particles may comprise a hydrogel, such as agarose, collagen, or fibrin.

Non-biodegradable or biodegradable polymers may be used to form the particles. In the preferred embodiment, the particles are formed of a biodegradable polymer. In general, synthetic polymers are preferred, although natural polymers may be used and have equivalent or even better properties, especially some of the natural biopolymers which degrade by hydrolysis, such as some of the polyhydroxyalkanoates. Representative synthetic polymers include poly(hydroxy acids) such as poly(lactic acid), poly(glycolic acid), and poly(lactic acid-co-glycolic acid), polyanhydrides, polyorthoesters, polyamides, polycarbonates, polyalkylenes such as polyethylene and polypropylene, polyalkylene glycols such as poly(ethylene glycol), polyalkylene oxides such as poly(ethylene oxide), polyalkylene terepthalates such as poly(ethylene terephthalate), polyvinyl alcohols, polyvinyl ethers, polyvinyl esters, polyvinyl halides such as poly(vinyl chloride), polyvinyl pyrrolidone, polysiloxanes, poly(vinyl alcohols), poly(vinyl acetate), polystyrene, polyurethanes and co-polymers thereof, derivativized celluloses such as alkyl cellulose, hydroxyalkyl celluloses, cellulose ethers, cellulose esters, nitro celluloses, methyl cellulose, ethyl cellulose, hydroxypropyl cellulose, hydroxypropyl methyl cellulose, hydroxybutyl methyl cellulose, cellulose acetate, cellulose propionate, cellulose acetate butyrate, cellulose acetate phthalate, carboxy-ethyl cellulose, cellulose triacetate, and cellulose sulfate sodium salt (jointly referred to herein as "synthetic celluloses"), polymers of acrylic acid, methacrylic acid or copolymers or derivatives thereof including esters, poly(methyl methacrylate), poly(ethyl methacrylate), poly(butylmethacrylate), poly(isobutyl methacrylate), poly(hexylmethacrylate), poly(isodecyl methacrylate), poly(lauryl methacrylate), poly(phenyl methacrylate), poly(methyl acrylate), poly(isopropyl acrylate), poly(isobutyl acrylate), and poly(octadecyl acrylate) (jointly referred to herein as "polyacrylic acids"), poly(butyric acid), poly(valeric acid), polycaprolactone and poly(lactide-co-capro-lactone), copolymers and blends thereof. As used herein, "derivatives" include polymers having substitutions, additions of chemical groups and other modifications routinely made by those skilled in the art.

Examples of preferred biodegradable polymers include polymers of hydroxy acids such as lactic acid and glycolic acid, and copolymers with PEG, poly-anhydrides, poly(ortho)esters, polyurethanes, poly(butyric acid), poly(valeric acid), poly-caprolactone, poly(lactide-co-caprolactone), blends and copolymers thereof.

Examples of preferred natural polymers include proteins such as albumin, collagen, gelatin and prolamines, for example, zein, and polysaccharides such as alginate, cellulose derivatives and polyhydroxyalkanoates, for example, polyhydroxybutyrate. The in vivo stability of the particles can be adjusted during the production by using polymers such as poly(lactide-co-glycolide) copolymerized with polyethylene glycol (PEG). If PEG is exposed on the external surface, it may increase the time these materials circulate due to the hydrophilicity of PEG.

While not intending to be bound by theory, the dependence of the instant peptides on chylomicron-forming lipid for absorption suggests a route through gut lymphatics. This unique gut lymphatic route, unlike the blood absorption, offers the advantage of bypassing the first-pass liver clearance. It is known that the flow rate of gut lymphatic absorption is only ~$1/500^{th}$ of that of blood absorption, which offers the advantage of slow oral absorption if it is so desired. Since degradable or releasable delivery vehicles can be engineered, drugs carried in such vehicles, particularly NPs or MPs, can be released in the gut lamina propria before entering gut lymphatics for faster blood absorption. Therefore, vehicles utilizing the targeting ligands can be made tunable in the distribution between blood and lymphatic routes and in the speed of absorption.

The size of the carrier may also modify the transport properties across the intestinal epithelium barrier. Gut lymphatics at the capillary end are known to have clefts that allow for one-way entry. It is known that the entry rate is inversely related to vehicle size. In a preferred embodiment, the increased micron size of the carrier or particle, will lead to a slower speed. A large sized particle will likely reside in gut lamina propria for days or weeks, offering a depot that slowly and constantly releases a therapeutic, biologic, or diagnostic agent to be circulated by the lymphatic system. This form of slow release is particularly useful to deliver potent, low concentration biomacromolecules such as interferon and insulin.

One of ordinary skill in the art will appreciate that there are numerous particle compositions that could be used in the presently described and claimed invention.

In some embodiments, the copolymer blocks of the carrier comprise polyethylene glycol (PEG) blocks and hydrophobic polymer blocks. The PEG blocks have multiple benefits like improving solubility of the peptide, preventing the hydrophobic amino acids of the ligand to interact with the core of nanoparticles, providing adequate flexibility for the ligand while engaged in receptor biding and/or lipid interactions as well as improving the viscoelastic parameters of the final particles.

Various technologies can be employed in preparing nanoparticles. In an exemplary embodiment, the nanoparticles (NPs) of the present invention are assembled using flash nanoprecipitation (FNP) technology. The process requires diblock co-polymers, consisting of a hydrophobic and a hydrophilic domain. Depending on the size of the individual domains and their size ratio the hydrodynamic radii of the NPs are falling between 25 and 100 nm, preferably between 40 and 75 nm resulting in particles of narrow size distribution (diameter=80-150 nm). Diblock copolymers of the present invention are exemplified in Table 2.

TABLE 2

| | | Diblock copolymers | | | |
|---|---|---|---|---|---|
| Polymer # | Hydrophobic block | Hydrophobic block size (kDa) | Hydrophilic block | Hydrophilic block size (kDa) | Biodegradable |
| 1 | Polystyrene | 1.5 | PEG | 5.0 | No |
| 2 | Polylactic acid | 5.0 | PEG | 4.0 | Yes |
| 3 | Polycaprolic acid | 6.5 | PEG | 5.0 | Yes |

B. Therapeutic Agents

Therapeutic agents may be bound to the peptide ligand of the present invention by known methods in the art (e.g., by covalent bond, noncovalent interactions, or expressed as a fusion or chimeric protein). A therapeutic agent or multiple therapeutic agents may be bound to a carrier, as well as multiple types of therapeutic agents. In a further embodiment a therapeutic agent may be bound to a carrier using a linker. For example, BIOCONJUGATE TECHNIQUES (Academic Press; 1st edition, Greg T. Hermanson, 1996) describes techniques for modifying or crosslinking of biomolecules. For example, a diagnostic agent and a pharmaceutically active agent may be bound to a peptide ligand of the present invention. In another example, multiple types of agents may be bound to a carrier, such as at least one pharmaceutically active agent, at least one biologic agent, at least one diagnostic agent and at least one targeting agent, or various combinations thereof.

Examples of pharmaceutically active therapeutic agents include drug compounds such as anti-infective agents, antibiotics, such as tetracyclines (e.g. minocycline), rifamycins (e.g. rifampin), macrolides (e.g. erythromycin), penicillins (e.g. nafcillin), cephalosporins (e.g. cefazolin), other beta-lactam antibiotics (e.g. imipenem, aztreonam), aminoglycosides (e.g. gentamicin), chloramphenicol, sulfonamides (e.g. sulfamethoxazole), glycol-peptides (e.g. vancomycin), quinolones (e.g. ciprofloxacin), fusidic acid, trimethoprim, metronidazole, clindamycin, mupirocin, polyenes (e.g. amphotericinB), azoles (e.g. fluconazole), betalactam inhibitors (e.g. sulbactam), minocycline, rifampin, erythromycin, nafcillin, cefazolin, imipenem, aztreonam, gentamicin, sulfamethoxazole, vancomycin, ciprofloxacin, trimethoprim, metronidazole, clindamycin, teicoplanin, mupirocin, azithromycin, clarithromycin, ofloxacin, lomefloxacin, norfloxacin, nalidixic acid, sparfloxacin, pefloxacin, amifloxacin, enoxacin, fleroxacin, temafloxacin, tosufloxacin, clinafloxacin, sulbactam, clavulanic acid, amphotericin B, fluconazole, itraconazole, ketoconazole, nystatin, anti-viral drugs, such as acyclovir and acyclovir prodrugs, famcyclovir, zidovudine, didanosine, stavudine, lamivudine, zalcitabine, saquinavir, saquinavir mesylate, indinavir, ritonavir, n-docosanol, tromantadine, idoxuridine, amprenavir, nelfinavir mesylate, tipranavir, darunavir, atazanavir sulfate, HIV antiviral agents, HIV protease inhibitors, HIV reverse transcriptase inhibitors, HIV integrase inhibitors, anti-fungal agents, such as amorolfine, isoconazole, clotrimazole, econazole, miconazole, nystatin, terbinafine, bifonazole, amphotericin, griseofulvin, ketoconazole, fluconazole, flucytosine, fezatione, ticlatone, tolnaftate, triacetin, zinc pyrithione, sodium pyrithione, steroidal anti-inflammatory drugs, NSAIDs and NSAID analogs, such as ibuprofen, flurbiprofen, ketoprofen, aclofenac, diclofenac, aloxiprin, aproxen, diflunisal, fenoprofen, indomethacin, mefenamic acid, naproxen, phenylbutazone, piroxicam, salicylamide, salicylic acids, sulindac, desoxysulindac, tenoxicam, tramadol, ketoralac, flufenisal, salsalate, triethanolamine salicylate, aminopyrine, antipyrine, oxyphenbutazone, apazone, cintazone, flufenamic acid, clonixerl, clonixin, mecloenamic acid, flunixin, coichicine, demecolcine, allopurinol, oxypurinol, benzydamine hydrochloride, dimefadane, indoxole, intrazole, mimbane hydrochloride, paranylene hydrochloride, tetrydamine, benzindopyrine hydrochloride, fluprofen, ibufenac, naproxol, fenbufen, cinchophen, diflumidone sodium, fenamole, flutiazin, metazamide, letimide hydrochloride, nexeridine hydrochloride, octazamide, molinazole, neocinchophen, nimazole, proxazole citrate, tesicam, tesimide, tolmetin, and triflumidate, oncology agents, such as sancycline, sancycline analogs, olvanil, olvanil analogs, retro-olvanil, retro-olvanil analogs, olvanil carbamate, budesonide, budesonide analogs, methylprednisolone, methylprednisolone analogs, dexamethasone, dexamethasone analogs, camptothecin, carboplatin, doxorubicin, paclitaxel, and the like.

4. Pharmaceutical Compositions

The present invention provides a pharmaceutical composition comprising the peptide ligands of the present invention and a therapeutic agent, and may include a pharmaceutically acceptable carrier for gastrointestinal administration, suitable for administration to a mammal, fish, bird, preferably a human. To administer the pharmaceutical composition to humans or animals, it is preferable to formulate the molecules in a composition comprising one or more pharmaceutically acceptable carriers. The phrase "pharmaceutically or pharmacologically acceptable" refers to molecular entities and compositions that do not produce allergic, or other adverse reactions when administered using routes well-known in the art. "Pharmaceutically acceptable carriers" include any and all clinically useful solvents, dispersion media, coatings, antibacterial and antifungal agents, isotonic and absorption delaying agents and the like.

Examples of pharmaceutically acceptable carriers or additives include water, a pharmaceutical acceptable organic solvent, collagen, polyvinyl alcohol, polyvinyl-pyrrolidone, a carboxyvinyl polymer, carboxymethylcellulose sodium, polyacrylic sodium, sodium alginate, water-soluble dextran, carboxymethyl starch sodium, pectin, methyl cellulose, ethyl cellulose, xanthan gum, gum Arabic, casein, gelatin, agar, diglycerin, glycerin, propylene glycol, polyethylene glycol, Vaseline, paraffin, stearyl alcohol, stearic acid, human serum albumin (HSA), mannitol, sorbitol, lactose, a pharmaceutically acceptable surfactant and the like. Additives used are chosen from, but not limited to, the above or combinations thereof, as appropriate, depending on the dosage form of the present invention.

In some embodiments there is provided a composition comprising the above described conjugate and a pharmaceutically acceptable carrier. The therapeutic agent admixed in the conjugate can be a pharmaceutically active, diagnostic, biologic, imaging or targeting agent.

The composition may further include an oil, fat or lipid. Non-limiting exemplary amount of the oil, fat or lip in a formulation dosage unit can be 10 mg, about 20 mg, about 30 mg, about 40 mg, about 50 mg, about 80 mg, about 100 mg, about 200 mg, about 400 mg, about 500 mg, about 800 mg, about 1 g, about 2 g, about 3 g, about 4 g, about 5 g, about 6 g, about 7 g, about 8 g, about 9 g, about 10 g, or about 15 g.

The composition of the present invention may also include a stabilizer including vitamin E, fat, wax, oil, and FDA approved supplement or additives.

Various technologies can be utilized to prepare dosage forms of the present invention. Table 3 exemplifies drug encapsulation by flash nanoprecipitation.

TABLE 3

| | | | | | | Polymer: | | | Drug |
| Drug | Type | LogP | Polymer | Conc. (mg/mL) | Encapsulating Agent | Core Ratio | Encapsulation Efficiency | Drug Loading | Amount (mg) |
| --- | --- | --- | --- | --- | --- | --- | --- | --- | --- |
| Ritonavir | Protease Inhibitor | 5.0 | PS-PEG | 15 | VitE alone | 1:1 | 48% | 16% | 7.5 |
| Darunavir | Protease Inhibitor | 1.8 | PCL-PEG | 10 | VES alone | 1:3 | 53% | 32% | 15.5 |
| Rilpivirine | Non-Nucleoside Reverse Transcriptase Inhibitor | 3.8 | PCL-PEG | 10 | VitE + VES | 1:1 | 85% | 12% | 2.0 |
| Dolutegravir | Integrase Inhibitor | 1.0 | PCL-PEG | 10 | VitE + $C_{12}$-$NH_2$ | 1:1 | 42% | 3% | 1.2 |
| Ciclopirox | TRAP agent | 2.2 | PCL-PEG | 20 | VitE + $C_{12}$-$NH_2$ | 1:1 | 39% | 11% | 6.3 |

HIV-1 drug encapsulation by Flash Nanoprecipitation (VES = Vitamin E succinate)

5. Nucleic Acids

The present invention also includes isolated nucleic acid sequences encoding the ligand peptides. In a further embodiment, the present invention provides for isolated nucleic acid sequences that encode SEQ ID NOS. 1-5. One with ordinary skill in the art can derive the nucleic sequence from the ligand peptide sequences disclosed.

In other related embodiments, the described invention provides polynucleotide variants that encode the ligand peptide sequences, SEQ ID NOs: 1-5, These polynucleotide variants have at least 70%, at least 75%, at least 80%, at least 85%, at least 90%, at least 95%, at least 96%, at least 97%, at least 98%, or at least 99%, or greater, sequence identity compared to a polynucleotide sequence of this invention, as determined using the methods described herein, (for example, BLAST analysis using standard parameters). One skilled in this art will recognize that these values can be appropriately adjusted to determine corresponding identity of proteins encoded by two nucleotide sequences by taking into account codon degeneracy, amino acid similarity, reading frame positioning, and the like.

The present invention provides a vector comprising a nucleic acid of the invention. The vector may be an expression vector. An expression vector may comprise additional elements. For example, the expression vector may have two replication systems allowing it to be maintained in two organisms, e.g., in mammalian or insect cells for expression and in a prokaryotic host for cloning and amplification. For integrating expression vectors, the expression vector may contain at least one sequence homologous to the host cell genome, and preferably two homologous sequences which flank the expression construct. The integrating vector may be directed to a specific locus in the host cell by selecting the appropriate homologous sequence for inclusion in the vector. The vector may also comprise a selectable marker gene to allow the selection of transformed host cells.

The present invention provides a host cell comprising a vector of the invention. The cell may be a bacterial, fungal, plant, insect or animal cell.

The present invention provides kits comprising an amino acid and/or nucleic acid of the invention together with any or all of the following: assay reagents, buffers, probes and/or primers, and sterile saline or another pharmaceutically acceptable emulsion and suspension base. In addition, the kits may include instructional materials containing directions (e.g., protocols) for the practice of the methods of this invention.

6. Method to Deliver a Therapeutic Agent and/or Carrier in Vivo

The present invention provides a method to deliver a therapeutic agent across the intestinal epithelial barrier in vivo. The examples herein disclosed exemplify a method of conjugating the peptide ligand of the present invention to a therapeutic agent. Accordingly, One with ordinary skill in the art can bind the peptide ligands of the present invention to a therapeutic agent of interest, and introduce the conjugate in vivo.

The present invention provides a method to deliver a carrier across the intestinal epithelial barrier in vivo. The examples herein disclosed exemplify a method of conjugating the peptide ligand of the present invention to an carrier. Accordingly, One with ordinary skill in the art can bind the peptide ligands of the present invention to an carrier of interest, and introduce the conjugate in vivo.

One with ordinary skill in the art can introduce the peptide ligand of the present invention bound to a therapeutic agent and/or carrier to an animal by gastrointestinal administration. Gastrointestinal embodiments include embodiments in which the peptide ligand of the present invention bound to a therapeutic agent and/or carrier and formulated for introduction to an animal in accordance with known methods for gastrointestinal delivery, such as by oral administration, rectal administration, and the like.

The dosage required depends on the choice of the route of administration, preferably oral administration; the nature of the formulation; the nature of the patient's illness; the subject's size, weight, surface area, age, and sex; other drugs being administered; and the judgment of the attending physician. Variations in the needed dosage are to be expected in view of the variety of agents available and the different efficiencies of various routes of administration. Variations in these dosage levels can be adjusted using standard empirical routines for optimization as is well understood in the art.

Oral dosage forms may include tablets and capsules. In particular examples, an oral dosage range is from about 1.0 to about 100 mg/kg body weight administered orally in single or divided doses, including from about 1.0 to about 50 mg/kg body weight, from about 1.0 to about 25 mg/kg body weight, from about 1.0 to about 10 mg/kg body weight (assuming an average body weight of approximately 70 kg; values adjusted accordingly for persons weighing more or less than average). For oral administration, the compositions are, for example, provided in the form of a tablet containing from about 50 to about 1000 mg of the active ingredient, particularly about 75 mg, about 100 mg, about 200 mg, about 400 mg, about 500 mg, about 600 mg, about 750 mg, or about 1000 mg of the active ingredient for the symptomatic adjustment of the dosage to the subject being treated.

In one embodiment, the rectal dosage form is an enema. In another embodiment, the rectal dosage form is a suppository. Variations in dosage levels can be adjusted using standard empirical routines for optimization as is well understood in the art.

EXAMPLES

The invention now being generally described, it will be more readily understood by reference to the following examples, which are included merely for purposes of illustration of certain aspects and embodiments of the present invention, and are not intended to limit the invention.

Example 1

Transport Across the Intestinal Epithelial Barrier

Fat is absorbed from the human gut in the form of chylomicrons, which are formed within intestinal epithelial cells from emulsified fat droplets absorbed from the intestinal lumen. The intestinal epithelial cells then secrete the chylomicrons to the abluminal (blood) side. Due to their micron-sizes, chylomicrons cannot enter the blood stream through the capillaries but rather they enter the gut lymphatics. In the instant invention, two lead peptides (SEQ ID NOS. 1 and 2) were isolated from a random 12-mer linear peptide library (size $1.2 \times 10^9$) using T7 phage display. These two peptides, when attached to nanoscale phage carriers, are able to cross Caco-2 cell monolayers in a chylomicron lipid-dependent manner. The Caco-2 monolayer is an in vitro model for the human intestinal epithelium. Each phage displays one sequence of a 12 residue linear peptide at about 10 copies per phage. Therefore, each peptide-displaying T7 phage can be viewed as an approximately a 65 nm spherical nanoparticle conjugated with peptides on its surface. As shown in FIG. 1, phages displaying peptides SEQ ID NOS. 1 and 2, cross Caco-2 monolayers in a chylomicron lipid-dependent manner. Compared to phages displaying several control peptides, the amount of phage nanoparticles translocated from the apical to the basolateral side is three-orders and two-orders of magnitude higher for SEQ ID NOS. 1 and 2 phage, respectively. The results demonstrate that nanoparticles with these peptides displayed on their surfaces will be absorbed after oral administration.

Three lead phages displaying peptides were sequenced to deduce the amino acid sequence of the displayed peptide, from the N-terminus to C-terminus. Their sequences shown below demonstrate that they share a structural feature of one or two ion-bridges formed by one or two pairs of charged residues (bold faced) flanking hydrophobic residues (shaded gray). Consequently, it is deduced that all three are amphipathic, or surfactant-like. SEQ ID NO. 3 is a phage genome rearrangement product and has 17 residues. SEQ ID NO. 3 is also less effective in crossing Caco-2 monolayers than SEQ ID NO. 1 (the best) and SEQ ID NO. 2 (the second best).

```
                                          (SEQ ID NO. 1)
19: TKWPVDMCPNVS (SEQ ID NO. 2)
12: QDDVQTWQRQPK (SEQ ID NO. 3)
23: GENFEQDWKSLRPHSSN.
```

Figure 2:
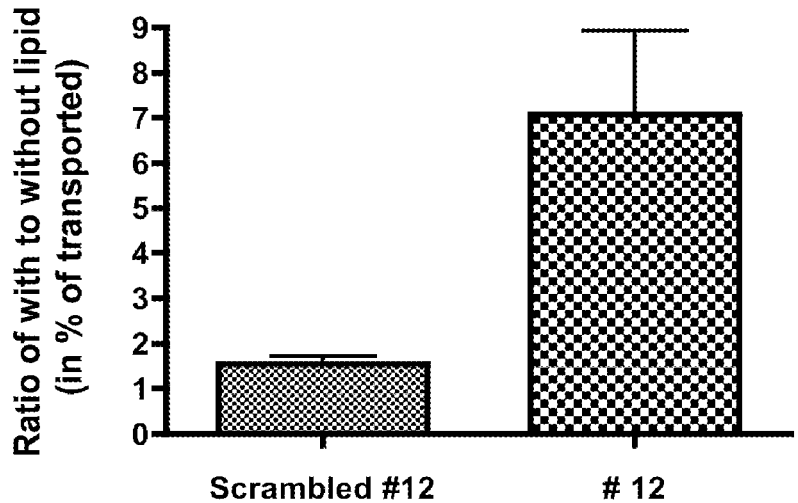
FIG. 2. Illustrates that peptide-labeled #12 (SEQ ID NO. 2) and its sequence-scrambled peptide FITC-12C1 were transported across Caco-2 intestinal epithelial monolayer in the presence and absence of chylomicron lipid-forming micelles.

Fluorescently labeled peptides according to SEQ ID NOS. 1 and 3 were synthesized. The peptide according to SEQ ID NO. 1 aggregated immediately after being diluted from DMSO stock into an aqueous solution. The peptide according to SEQ ID NO. 2 did not show this phenomenon by the naked eye but light aggregation was still detected in a particle analyzer with aggregate size showing a sharp peak at 2 nm. Therefore, the peptide according to SEQ ID NO. 2 aggregate may be viewed as a small nanoparticle displaying some peptides according to SEQ ID NO. 2 in correct orientation (i.e., on the surface not buried inside the nanoparticle). Even with this imperfect display, some increase in chylomicron lipid-dependent translocation across Caco-2 monolayers is still noticeable over a scrambled peptide according to SEQ ID NO. 1 (12C1) (FIG. 2). FITC-12 was 4.6-fold more efficiently transported than the sequence-scrambled control (FIG. 2). Student t test indicates that the difference between the two is statistically significant (n=3, $p<0.05$).

Figure 3:
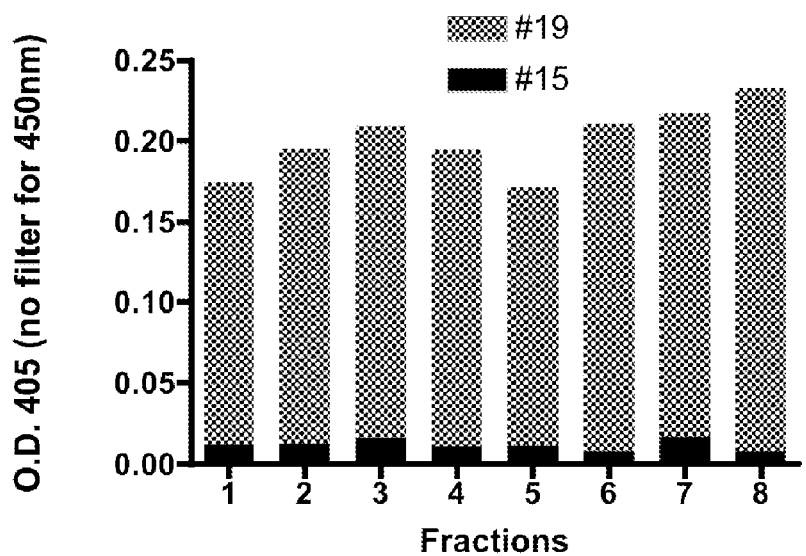
FIG. 3. Illustrates a comparison of ApoB48 levels in fractions of Caco-2 basolateral side medium.

In addition, phage displaying a peptide according to SEQ ID NO. 1, but not a negative control peptide, dramatically induces ApoB48 production (FIG. 3). ApoB48 is a marker and component of chylomicron. Caco-2 monolayers were incubated with phage displaying the best lead peptide (SEQ ID NO. 1) or a negative phage clone (#15 in FIG. 3). The negative phage clone was randomly picked up among a number of negative phage clones, all showing the same baseline transport rate as the starting library phages, a mixture of phages displaying 1.2 billion different peptide sequences. The control shows only base level signal. Thus, the data indicates that (a) it is the displayed lead peptides, not the phage capsid protein, that confer a nanoparticle the ability to cross Caco-2 monolayer and (b) transport across gut epithelial cells is likely chylomicron-dependent.

The specification is most thoroughly understood in light of the teachings of the references cited within the specification. The embodiments within the specification provide an illustration of embodiments of the invention and should not be construed to limit the scope of the invention. The skilled artisan readily recognizes that many other embodiments are encompassed by the invention. All publications, and patents, cited in this disclosure are incorporated by reference in their entirety. To the extent the material incorporated by reference contradicts or is inconsistent with this specification, the specification will supersede any such material. The citation of any references herein is not an admission that such references are prior art to the present invention.

Those skilled in the art will recognize, or be able to ascertain using no more than routine experimentation, many equivalents to the specific embodiments of the invention described herein. Such equivalents are intended to be encompassed by the following embodiments.

The invention claimed is:

1. A conjugate comprising one or more peptide ligands attached to a nanoparticle carrier, wherein:

said nanoparticle carrier comprises a hydrophobic therapeutic agent admixed with a biocompatible block copolymer comprising polyethylene glycol (PEG) blocks and hydrophobic polymer blocks;

said peptide ligand consists of an amino acid sequence wherein 1-2 pairs of amino acids are of an opposite charge, the members of said pair are separated by a spacer consisting of 1-12 amino acid residues comprising at least one hydrophobic amino acid, and the length of said amino acid sequence is greater than 5 and less than 20 amino acids; and wherein the first member of each of said pairs is selected from the group consisting of D and E, and the second member of opposite charge is independently selected from the group consisting of K, R, and H;

each peptide ligand is attached to said nanoparticle through conjugation to a block copolymer of said nanoparticle by covalent bonding to a PEG block; and said conjugate has an average diameter between about 1 and about 700 nm;

wherein said amino acid sequence is at least 75% identical to SEQ ID NO: 4 or at least 75% identical to SEQ ID NO: 5, and wherein further, non-identical amino acids are conservative substitutions of corresponding residues of SEQ ID NO: 4 or SEQ ID NO: 5; and wherein said amino acid sequence comprises a salt bridge which allows the peptide ligand to function as a carrier as a result of the amphiphilic conformation maintained by said salt bridge to allow the conjugate to be associated with, or incorporated into, lipid micelles.

2. The conjugate of claim 1, wherein said hydrophobic polymer is selected from the group consisting of poly(lactic acid), poly(lactic acid-co-glycolic acid), polycaprolactone, polyanhydrides, polyorthoesters, polyamides, polycarbonates, polyalkylenes, poly-alkylene terepthalates, polyvinyl halides, polysiloxanes, poly(vinyl acetate), polystyrene, polyurethanes, synthetic celluloses, polyacrylic acids, poly(butyric acid), poly(valeric acid), poly(lactide-co-capro-lactone) and combinations thereof.

3. The conjugate of claim 1, characterized by an average diameter of equal to or greater than about 500 nm.

4. The conjugate of claim 1, characterized by an average diameter of between about 50-500 nm.

5. The conjugate of claim 4, further comprising a targeting agent selected from the group consisting of RGD peptide, EGF peptide, DV3 peptide, an LYP peptide, a membrane-binding domain of IGFBP3, fMLF, mannose, transferrin ligand, monoclonal anti-bodies, and drug conjugated derivatives thereof.

6. The conjugate of claim 1, characterized by an average diameter of smaller than about 10 nm.

7. The conjugate of claim 6, further comprising a targeting agent selected from the group consisting of RGD peptide, EGF peptide, DV3 peptide, an LYP peptide, a membrane-binding domain of IGFBP3, fMLF, mannose, transferrin ligand, monoclonal anti-bodies, and drug conjugated derivatives thereof.

8. The conjugate of claim 1, wherein said peptide ligand is bound to said nanoparticle via a linkage selected from the group consisting of an amide, a thio ether, a 1,2,3-triazole.

9. The conjugate of claim 1, wherein said peptide ligand comprises a monodisperse PEG block.

10. The conjugate of claim 1, wherein said amino acid sequence is at least 75% identical to SEQ ID NO: 4, wherein further, non-identical amino acids are conservative substitutions of corresponding residues of SEQ ID NO: 4.

11. The conjugate of claim 1, wherein said amino acid sequence is at least 75% identical to SEQ ID NO: 5, and wherein further, non-identical amino acids are conservative substitutions of corresponding residues of SEQ ID NO: 5.

12. The conjugate of claim 1, wherein the therapeutic agent is a pharmaceutical active, diagnostic, biologic, imaging or targeting agent.

13. A composition comprising the conjugate of claim 1 and a pharmaceutically acceptable carrier.

14. The composition according to claim 13, wherein the therapeutic agent is a pharmaceutical active, diagnostic, biologic, imaging or targeting agent.

15. The composition of claim 13, wherein said conjugate has an average diameter of between about 50-500 nm and said composition further comprises a fat or oil.

16. The composition of claim 13, further comprising a stabilizer selected from vitamin E, fat, wax, and oil.

17. The composition of claim 14, wherein said pharmaceutical active agent is selected from the group consisting of tetracyclines, rifamycins, macrolides, penicillins, cephalosporins, beta-lactam antibiotics, aminoglycosides, chloramphenicol, sulfamethoxazole, vancomycin, ciprofloxacin, fusidic acid, trimethoprim, metronidazole, clindamycin, mupirocin, amphotericinB, fluconazole, sulbactam, minocycline, rifampin, erythromycin, nafcillin, cefazolin, imipenem, aztreonam, gentamicin, sulfamethoxazole, vancomycin, ciprofloxacin, trimethoprim, metronidazole, clindamycin, teicoplanin, mupirocin, azithromycin, clarithromycin, ofloxacin, lomefloxacin, norfloxacin, nalidixic acid, sparfloxacin, pefloxacin, amifloxacin, enoxacin, fleroxacin, temafloxacin, tosufloxacin, clinafloxacin, sulbactam, clavulanic acid, amphotericin B, fluconazole, itraconazole, ketoconazole, nystatin, acyclovir, acyclovir prodrugs, famcyclovir, zidovudine, didanosine, stavudine, lamivudine, zalcitabine, saquinavir, indinavir, ritonavir, n-docosanol, tromantadine, idoxuridine, amorolfine, isoconazole, clotrimazole, econazole, miconazole, nystatin, terbinafine, bifonazole, amphotericin, griseofulvin, keto-conazole, fluconazole, flucytosine, fezatione, ticlatone, tolnaftate, triacetin, zinc pyrithione, sodium pyrithione, steroidal anti-inflammatory compounds, ibuprofen, flurbiprofen, ketoprofen, aclofenac, diclofenac, aloxiprin, aproxen, diflunisal, fenoprofen, indomethacin, mefenamic acid, naproxen, phenylbutazone, piroxicam, salicylamide, salicylic acid, sulindac, desoxysulindac, tenoxicam, tramadol, ketoralac, flufenisal, salsalate, triethanolamine salicylate, aminopyrine, antipyrine, oxyphenbutazone, apazone, cintazone, flufenamic acid, clonixerl, clonixin, meclofenamic acid, flunixin, coichicine, demecolcine, allopurinol, oxypurinol, benzydamine hydrochloride, dimefadane, indoxole, intrazole, mimbane hydrochloride, paranylene hydrochloride, tetrydamine, benzindopyrine hydrochloride, fluprofen, ibufenac, naproxol, fenbufen, cinchophen, diflumidone sodium, fenamole, flutiazin, metazamide, letimide hydrochloride, nexeridine hydrochloride, octazamide, molinazole, neocinchophen, nimazole, proxazole citrate, tesicam, tesimide, tolmetin, triflumidate, sancycline, sancycline analogs, olvanil, olvanil analogs, retro-olvanil, retro-olvanil analogs, olvanil carbamate, budesonide, budesonide analogs, methylprednisolone, methylprednisolone analogs, dexamethasone, dexamethasone analogs, camptothecin, carboplatin, doxorubicin, paclitaxel, saquinavir mesylate, amprenavir, ritonavir, indinavir, nelfinavir mesylate, tipranavir, rilpivirine, dolutegravir, ciclopirox, darunavir and atazanavir sulfate.

18. A method for the gastrointestinal delivery of a therapeutic agent with poor gastrointestinal absorption to a patient in need thereof, comprising administering to said patient a composition according to claim 15 by oral administration.

19. A peptide ligand comprising an amino acid sequence wherein 1-2 pairs of amino acids are of an opposite charge, the members of said pair are separated by a spacer consisting of 1-12 amino acid residues comprising at least one hydrophobic amino acid, the length of said amino acid sequence is greater than 5 and less than 20 amino acids, and said peptide ligand is bound to a monodisperse PEG block, wherein the first member of said pair of amino acids of said amino acid sequence is selected from the group consisting of D and E, and said second member of opposite charge is independently selected from the group consisting of K, R, and H;
   wherein said amino acid sequence is at least 75% identical to SEQ ID NO: 4 or at least 75% identical to SEQ ID NO: 5, and wherein further, non-identical amino acids are conservative substitutions of corresponding residues of SEQ ID NO: 4 or SEQ ID NO: 5; and
   wherein said amino acid sequence comprises a salt bridge which allows the peptide ligand to function as a carrier as a result of the amphiphilic conformation maintained by said salt bridge for association with, or incorporation into, lipid micelles.

20. The peptide ligand of claim 19, wherein said amino acid sequence comprises two pairs of amino acids of opposite polarity.

21. The peptide ligand of claim 19, wherein said amino acid sequence is at least 75% identical to SEQ ID NO: 4, and wherein further, non-identical amino acids are conservative substitutions of corresponding residues of SEQ ID NO: 4.

22. The peptide ligand of claim 19, wherein said amino acid sequence is at least 75% identical to SEQ ID NO: 5, and wherein further, non-identical amino acids are conservative substitutions of corresponding residues of SEQ ID NO: 5.

23. The peptide ligand of claim 19, wherein the monodisperse PEG unit has a molecular weight of less than about 500.

* * * * *

SEQUENCE LISTING

```
<160> NUMBER OF SEQ ID NOS: 5

<210> SEQ ID NO 1
<211> LENGTH: 12
<212> TYPE: PRT
<213> ORGANISM: Artificial
<220> FEATURE:
<223> OTHER INFORMATION: Peptide ligand

<400> SEQUENCE: 1

Thr Lys Trp Pro Val Asp Met Cys Pro Asn Val Ser
1               5                   10

<210> SEQ ID NO 2
<211> LENGTH: 12
<212> TYPE: PRT
<213> ORGANISM: Artificial
<220> FEATURE:
<223> OTHER INFORMATION: Peptide ligand
```

-continued

```
<400> SEQUENCE: 2

Gln Asp Asp Val Gln Thr Trp Gln Arg Gln Pro Lys
1               5                   10

<210> SEQ ID NO 3
<211> LENGTH: 17
<212> TYPE: PRT
<213> ORGANISM: Artificial
<220> FEATURE:
<223> OTHER INFORMATION: Peptide ligand

<400> SEQUENCE: 3

Gly Glu Asn Phe Glu Gln Asp Trp Lys Ser Leu Arg Pro His Ser Ser
1               5                   10                  15

Asn

<210> SEQ ID NO 4
<211> LENGTH: 6
<212> TYPE: PRT
<213> ORGANISM: Artificial
<220> FEATURE:
<223> OTHER INFORMATION: Peptide ligand

<400> SEQUENCE: 4

Thr Lys Trp Pro Val Asp
1               5

<210> SEQ ID NO 5
<211> LENGTH: 9
<212> TYPE: PRT
<213> ORGANISM: Artificial
<220> FEATURE:
<223> OTHER INFORMATION: Peptide ligand

<400> SEQUENCE: 5

Thr Lys Trp Pro Val Asp Met Cys Pro
1               5
```